(12) United States Patent
Shimizu

(10) Patent No.: US 6,747,186 B2
(45) Date of Patent: Jun. 8, 2004

(54) WATER-DECOMPOSABLE ABSORBENT ARTICLE

(75) Inventor: Jyoji Shimizu, Kagawa (JP)

(73) Assignee: Uni-Charm Corporation, Kawanoe (JP)

(*) Notice: Subject to any disclaimer, the term of this patent is extended or adjusted under 35 U.S.C. 154(b) by 0 days.

(21) Appl. No.: 09/886,505

(22) Filed: Jun. 21, 2001

(65) Prior Publication Data

US 2002/0013559 A1 Jan. 31, 2002

(30) Foreign Application Priority Data

Jun. 28, 2000 (JP) .................................. 2000-193813
May 7, 2001 (JP) .................................. 2001-135784

(51) Int. Cl.$^7$ .................................. A61F 13/15
(52) U.S. Cl. .................. 604/364; 604/375; 604/376; 604/366; 604/385.03; 604/385.23; 604/385.14
(58) Field of Search .................. 604/364, 317, 604/345, 356, 358, 365, 366, 367, 368, 369, 374, 375, 376, 385.03, 385.05, 385.14, 385.23, 386, 387, 389

(56) References Cited

U.S. PATENT DOCUMENTS

| | | | |
|---|---|---|---|
| 2,639,239 A | * 5/1953 | Elliot | 106/172.1 |
| 3,563,241 A | * 2/1971 | Evans et al. | 160/169 |
| 3,589,364 A | * 6/1971 | Dean et al. | 604/368 |
| 3,618,607 A | * 11/1971 | Ells et al. | 604/368 |
| 3,665,923 A | * 5/1972 | Champaigne, Jr. | 604/364 |
| 3,723,413 A | * 3/1973 | Chatterjee et al. | 427/180 |
| 3,731,686 A | * 5/1973 | Chatterjee | 536/87 |
| 3,756,232 A | * 9/1973 | Noguchi et al. | 604/359 |
| 3,858,585 A | * 1/1975 | Chatterjee | 604/376 |
| 3,965,091 A | * 6/1976 | Holst et al. | 525/54.3 |
| 4,090,013 A | * 5/1978 | Ganslaw et al. | 260/DIG. 47 |
| 4,187,342 A | * 2/1980 | Holst et al. | 442/417 |
| 4,200,557 A | * 4/1980 | Chatterjee et al. | 525/54.23 |
| 4,340,731 A | * 7/1982 | Colombo et al. | 536/87 |
| 4,357,938 A | * 11/1982 | Ito et al. | 604/376 |
| RE31,323 E | * 7/1983 | Marder et al. | 536/87 |
| 4,401,813 A | * 8/1983 | Lowell et al. | 536/98 |
| 4,650,716 A | * 3/1987 | Gelman | 428/402 |
| 4,664,105 A | * 5/1987 | Dautzenberg et al. | 424/400 |
| 4,710,184 A | * 12/1987 | Ehret | 604/265 |
| 4,940,785 A | * 7/1990 | Stober et al. | 536/90 |
| 5,300,358 A | * 4/1994 | Evers | 442/396 |
| 5,676,964 A | * 10/1997 | Della Valle et al. | 424/423 |
| 5,731,083 A | * 3/1998 | Bahia et al. | 428/393 |
| 5,801,116 A | * 9/1998 | Cottrell et al. | 502/401 |
| 6,432,095 B1 | * 8/2002 | Wada et al. | 604/385.01 |
| 6,433,245 B1 | * 8/2002 | Bjorkquist et al. | 604/364 |

FOREIGN PATENT DOCUMENTS

| | | | |
|---|---|---|---|
| EP | 0802282 | 10/1997 | .......... D21H/17/26 |
| EP | 0900878 | 3/1999 | .......... D21H/17/26 |
| JP | 3008897 | 1/1991 | |
| JP | 3167400 | 7/1991 | |
| JP | 6192991 | 7/1994 | |
| JP | 08-019571 | 1/1996 | |
| JP | 08-038547 | 2/1996 | |

* cited by examiner

*Primary Examiner*—Henry Bennett
*Assistant Examiner*—Kathryn Odland
(74) *Attorney, Agent, or Firm*—Darby & Darby

(57) ABSTRACT

Provided is an absorbent article which includes a backsheet, a liquid-pervious topsheet and an absorbent core sandwiched between the backsheet and the topsheet. At least the backsheet is made from a water-decomposable material. The backsheet is formed of a fibrous sheet that contains water-dispersible fibers and water-insoluble carboxymethyl cellulose. The water-insoluble carboxymethyl cellulose has a degree of etherification (D.S.) falling between 0.3 and 0.6, and is modified so that the hydrogens of at least 95% of carboxylic acids therein are substituted with metal.

6 Claims, 3 Drawing Sheets

WATER-DECOMPOSABLE ABSORBENT ARTICLE

BACKGROUND OF THE INVENTION

1. Field of the Invention

The present invention relates to an absorbent article for pantiliners, sanitary napkins, incontinence pads, diapers, etc., more particularly, to such an absorbent article having a water-decomposable backsheet.

2. Description of the Related Art

Recently, the absorbent articles such as the pantiliners and sanitary napkins disposable in flush toilets have come available. For example, Japanese Unexamined Patent Publication (Kokai) Nos. Heisei 8-38547 and 8-19571 disclose water-decomposable absorbent articles comprising a water-decomposable absorbent core and water-decomposable topsheet and backsheet between which the absorbent core is sandwiched.

The water-decomposable absorbent articles such as pantiliners and sanitary napkins have respectively an adhesive layer formed on the rear surface of the backsheet for fitting the absorbent article to an external support such as an undergarment. After used, the absorbent articles are peeled from external supports at the adhesive layer, and disposed of in flush toilets.

These water-decomposable absorbent articles are composed of constituent components (absorbent core, topsheet, backsheet, etc.) having increased decomposability in water. However, the conventional water-decomposable components of such absorbent articles are generally problematic in that, when their decomposability in water is increased, the bonding strength of fibers constituting them tends to be inevitably lowered in wet and dry condition. Therefore, it is difficult to increase both the decomposability in water and the strength of the water-decomposable components of absorbent articles.

In pantiliners and sanitary napkins having an adhesive layer on the backsheet for fitting them to external supports, when the backsheet is made from a water-decomposable material, the bonding strength between the backsheet and the adhesive layer is lowered. As a result, when the absorbent articles are, after used, peeled from external supports, the adhesive layer is often peeled from the backsheet to remain on external supports, and, in addition, the fibers constituting the backsheet may adhere to and remain on external supports along with the adhesive layer.

In such pantiliners and sanitary napkins, if the strength of the backsheet is low, it will cause another problem in that, when the basic weight (Metsuke) of the backsheet is reduced and the thickness thereof is reduced, the backsheet will lose the function of retaining the shape of the absorbent articles while they are worn, so that the absorbent articles may be deformed or distorted.

SUMMARY OF THE INVENTION

An object of the present invention is to provide an absorbent article of which the backsheet is decomposable in water and satisfies the two requirements of high decomposability in water and good surface strength enough for use.

According to an aspect of the invention, an absorbent article may comprise a backsheet, a liquid-pervious topsheet and a water-decomposable absorbent core sandwiched between the backsheet and the topsheet, at least the backsheet being made from a water-decomposable material, wherein;

the backsheet is formed of a fibrous sheet that contains water-dispersible fibers and water-insoluble carboxymethyl cellulose, and the water-insoluble carboxymethyl cellulose has a degree of etherification (D.S.) falling between 0.3 and 0.6, and is modified so that the hydrogens of at least 95% of carboxylic acids therein are substituted with metal.

In the absorbent article of the invention, the backsheet is formed of a fibrous sheet of which the surface strength and the breaking strength in the direction of the thickness are both high. Therefore, the backsheet surely retains the shape thereof during being used. Furthermore, when the absorbent article is, after used, peeled from an external support at the adhesive layer formed on the rear surface of the backsheet, the backsheet is not separated from the adhesive layer so that the backsheet hardly remains on the external support fitting with the adhesive layer. The breaking strength in the direction of the thickness of the backsheet is meant to indicate the breaking resistance of a fibrous sheet forming the backsheet in the direction of the thickness, when a tensile force is applied to the sheet in the vertically opposite directions so as to separate the front surface from the rear surface thereof.

For example, the metal is at least one selected from the group consisting of calcium, sodium, magnesium, zinc, manganese, lithium, barium, and aluminium.

In case where an adhesive layer for securing the absorbent article to an external support is formed on the rear side of the backsheet, the present invention produces better results.

The basic weight of the fibrous sheet to form the backsheet falls, for example, between 10 and 50 $g/m^2$.

Preferably, the water-insoluble carboxymethyl cellulose accounts for from 1 to 30% by weight of the fibrous sheet to form the backsheet.

Also preferably, the fibrous sheet to form the backsheet is a water-decomposable nonwoven fabric having been subjected to water-jetting treatment, or it is water-decomposable paper.

Also preferably, the water-dispersible fibers are fibers of at least one selected from the group consisting of pulp, regenerated cellulose, abaca, and linter pulp.

Also preferably, the fibrous sheet to form the backsheet has a surface strength of at least 4 (in terms of wax number), measured according to JIS P8129-1976 2.1.

DESCRIPTION OF THE PREFERRED EMBODIMENTS

Figure 1:
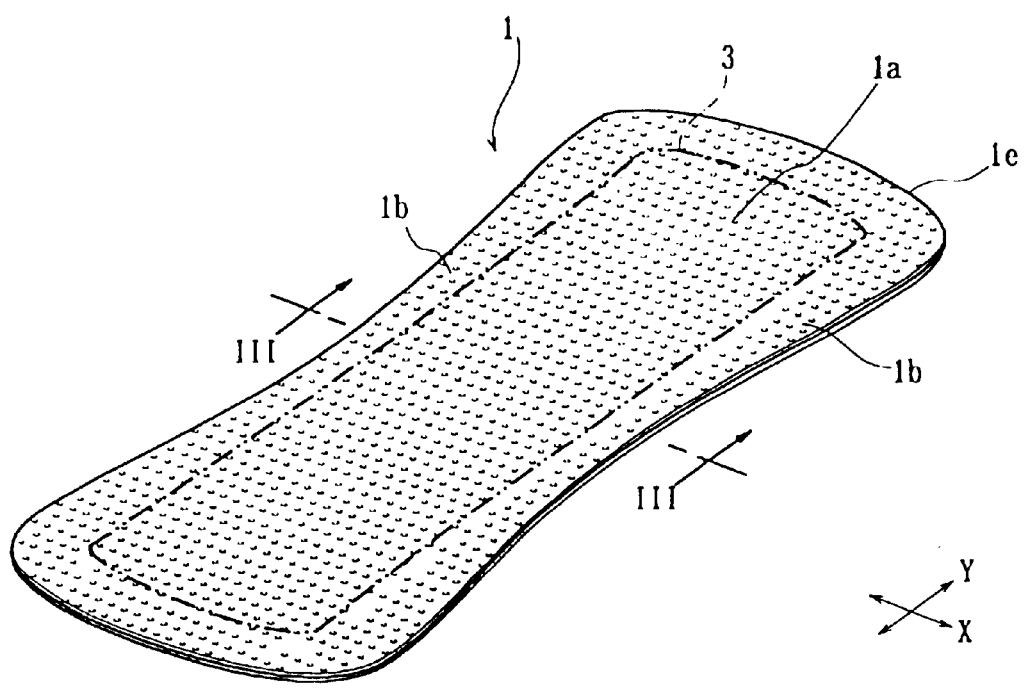
FIG. 1 is a perspective view of one embodiment of an absorbent article of the invention.
Figure 2:
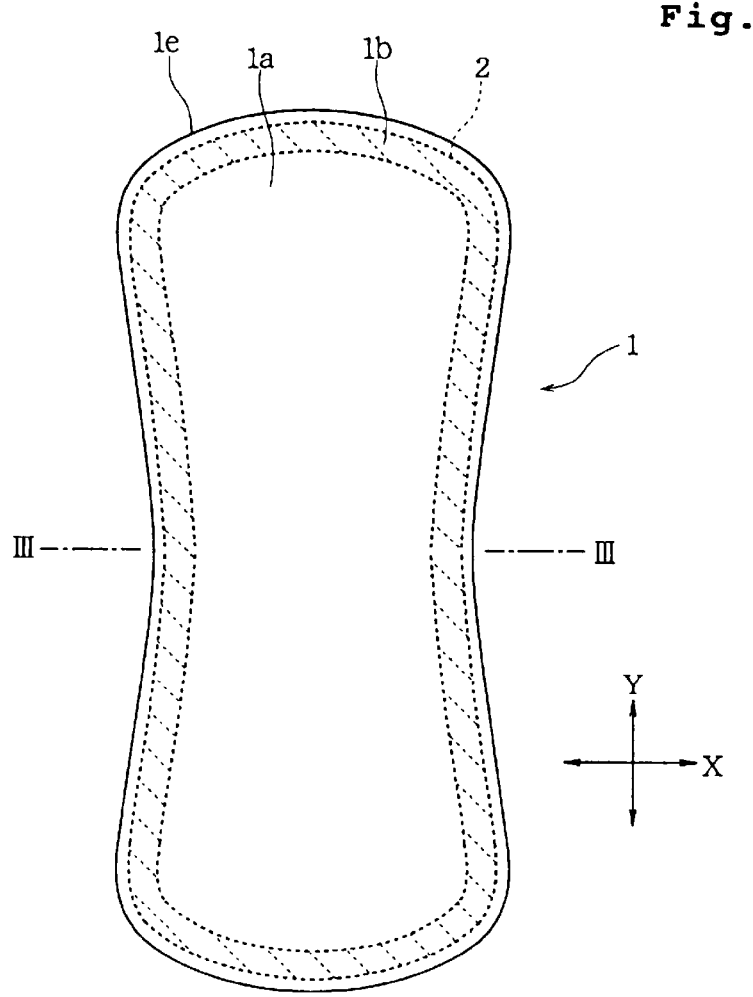
FIG. 2 is a top view of the absorbent article of FIG. 1.
Figure 3:
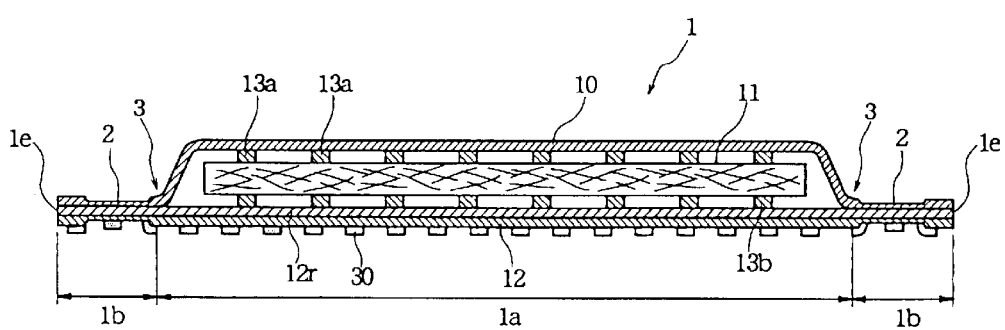
FIG. 3 is a cross-sectional view of the absorbent article of FIGS. 1 and 2, as taken along the line III—III.
Figure 4:
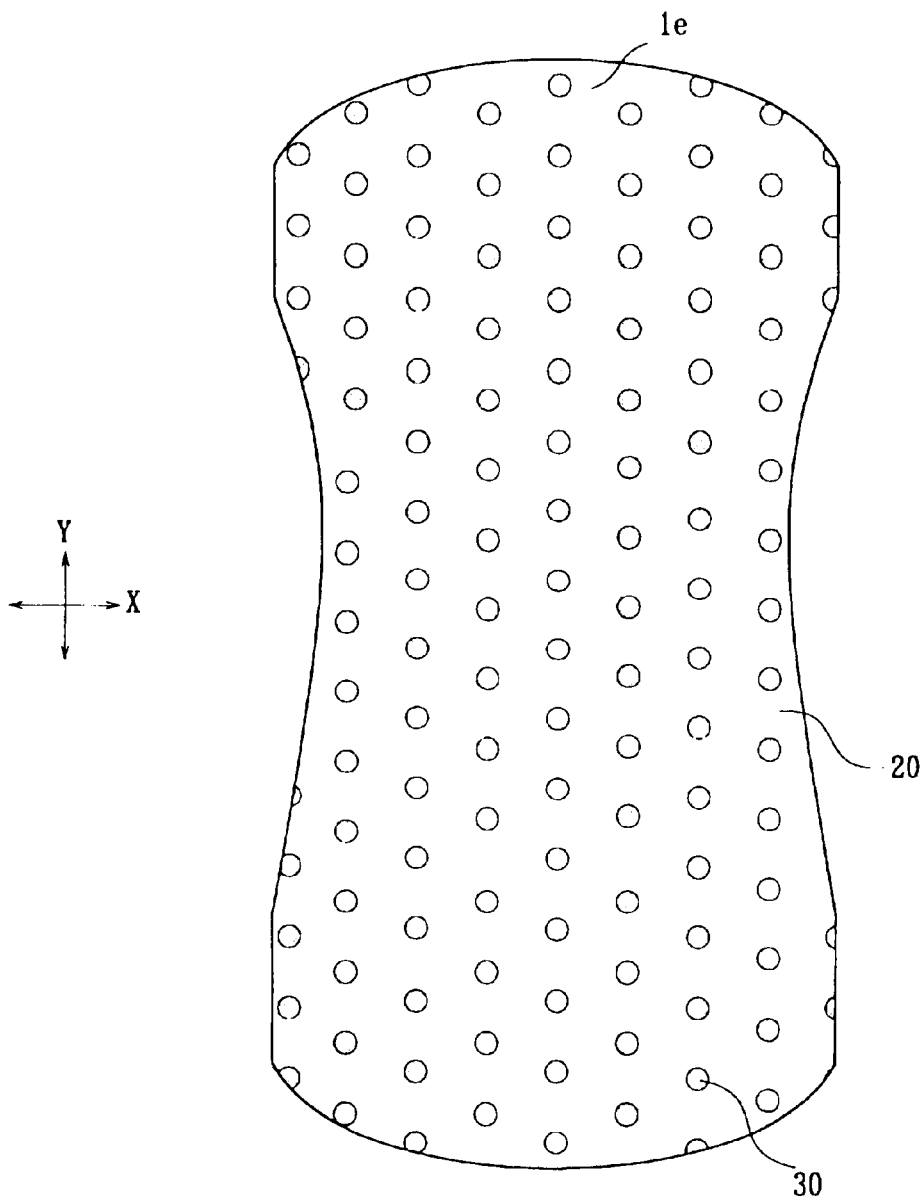
FIG. 4 is a bottom view of the absorbent article of FIGS. 1 and 2.

The invention will be described with reference to the accompanying drawings. FIG. 1 is a perspective view of one embodiment of an absorbent article of the invention, as viewed from a top surface thereof (i.e., a body facing surface that faces the skin of a wearer); FIG. 2 is a top view of the absorbent article of FIG. 1; FIG. 3 is a cross-sectional view of the absorbent article of FIGS. 1 and 2, as taken along the line III—III; and FIG. 4 is a bottom view of the absorbent article of FIGS. 1 and 2, as viewed from a back surface (i.e., a garment facing surface). In these, a longitudinal direction of the absorbent article is designated by Y, and a transverse direction which is substantially perpendicular to the direction Y is designated by X.

The absorbent article shown in FIGS. 1 and 2 is for pantiliners or sanitary napkins. As shown in FIG. 3, an absorbent article 1 comprises a liquid-pervious topsheet 10 that faces the skin of a wearer; a backsheet 12; and an absorbent core 11 sandwiched between the topsheet 10 and the backsheet 12.

In the absorbent article 1 of the invention, at least the backsheet 12 is formed of a water-decomposable material of fibers that are dispersible when having received a large amount of water. In the absorbent article 1 of the invention, the topsheet 10 and the absorbent core 11 are not necessarily required to be formed of a water-decomposable material, but are preferably formed of natural fibers or a biodegradable material. More preferably, the topsheet 10 and the absorbent core 11 are also decomposable in water.

As shown in FIG. 3, a thermoplastic resin layer 12r is applied to the absorbent core side of the backsheet 12. The region having a predetermined width between a peripheral edge 1e of the absorbent article 1 and a boundary 3 and extending along the periphery of the absorbent article 1, provides a peripheral region 1b. The boundary 3 is an inner edge of the peripheral region 1b. The peripheral region 1b is partly or entirely round-sealed to form a round-sealed area 2. Concretely, the peripheral region 1b of the absorbent article 1 is hot-pressed with surrounding the absorbent core 11 so that the water-soluble thermoplastic resin layer 12r in the region is fused to bond the topsheet 10 and the backsheet 12 therein, thereby forming the round-sealed area 2. In an intermediate region 1a inside of the boundary 3, adhesives 13a and 13b are dispersed in spiral or polka-dot pattern at a predetermined interval in the entire area between the constituent components of the absorbent article 1, i.e., between the top sheet 10 and the absorbent core 11, and between the absorbent core 11 and the thermoplastic resin layer 12r on the backsheet 12 to be bonded therebetween.

As shown in FIG. 3 and FIG. 4, an adhesive layer 30 for fitting the absorbent article 1 to an external support while in use is formed on the rear side of the backsheet 12. The adhesive layer 30 is a pressure-sensitive adhesive layer, and the surface thereof is covered with a release sheet for protecting the adhesive layer before use. Upon using the absorbent article 1, the release sheet is peeled from the absorbent article 1, and then the absorbent article 1 is fitted to a crotch part of the external support such as sanitary panties so that the adhesive layer 30 formed on the rear side of the absorbent article 1 is adhered and secured to the inner surface of the crotch part.

After used, the absorbent article 1 is removed from the external support at the adhesive layer 30, and then disposed of in a flush toilet. When the absorbent article 1 having been thus disposed of in a flush toilet has received a large amount of water therein and in a septic tank, the water-soluble thermoplastic resin 12r dissolves in water to release the backsheet 12, and then the fibers constituting the backsheet 12 are individually dispersed in water. In case where the topsheet 10 and the absorbent core 11 are both formed of the water-decomposable material, the topsheet 10 and the absorbent core 11 also are separately dispersed in water after the absorbent article 1 has been disposed of in a flush toilet.

The fibrous sheet for forming the backsheet 12 will be described in detail. The fibrous sheet comprises water-dispersible fibers and water-insoluble carboxymethyl cellulose that serves as a binder for binding the fibers. In place of water-insoluble carboxymethyl cellulose, the fibrous sheet may comprise carboxyethyl cellulose.

The water-dispersible fibers in the invention are meant to indicate fibers well dispersible in water. The terminology "water-dispersible" referred to herein for fibrous sheets is equal to "water-decomposable", and it means that the fibers constituting the fibrous sheet are individually dispersed in water when the sheet has received a large amount of water.

The water-dispersible fibers for use in the invention may be natural fibers and/or chemical fibers. Natural fibers usable herein include fibers of wood pulp (e.g., hardwood pulp, softwood pulp), abaca, kenaf or linter pulp; and chemical fibers also usable herein include regenerated fibers of rayon or fibrillated rayon, synthetic fibers of polypropylene, polyvinyl alcohol, polyester or polyacrylonitrile, and biodegradable synthetic fibers such as polylactic acid fibers, etc. Among those, preferred for use herein are biodegradable fibers such as natural fibers of pulp or kenaf, as well as rayon fibers or polylactic acid fibers. More preferred are natural fibers of pulp having a degree of beating of at most 700 cc, desirably at most 600 cc, as well as rayon fibers, as they are well dispersible in water.

Preferably, the fiber length of the water-dispersible fibers is at most 20 mm in view of the decomposability in water of the fibrous sheet. More preferably, it falls between 2 and 10 mm. In case where the water-dispersible fibers are of rayon, it is desirable that the fineness thereof falls between 1.1 and 3.3 dtex.

The fibrous sheet for use in the invention comprises water-insoluble carboxymethyl cellulose that serves as a binder. The water-insoluble carboxymethyl cellulose has a degree of etherification (D.S.) falling between 0.3 and 0.6. Preferably, its pH is at least 5.0.

Also preferably, the water-insoluble carboxymethyl cellulose is a completely-substituted compound in which hydrogens of at least 95%, more preferably at least 99.0%, even more preferably at least 99.9% of carboxylic acids are substituted with metal. Specifically, the preferred water-insoluble carboxymethyl cellulose is represented by the following chemical formula, wherein M of at least 95% of the carboxylic acid group (surrounded by the dotted line) is a metal and M of smaller than 5% of the carboxylic acid group is hydrogen.

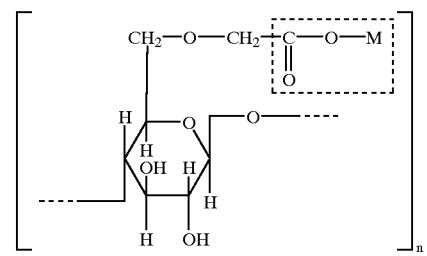

Preferably, the metal is at least one selected from the group consisting of calcium, sodium, magnesium, zinc, manganese, lithium, barium and aluminium. Among those, more preferred is calcium and/or sodium.

In the fibrous sheet, the water-insoluble carboxymethyl cellulose that serves as a binder is a completely-substituted (or substantially completely-substituted) compound. Accordingly, the hydrogen-bonding force (or the ester-bonding force) of the residual carboxylic acid (in which M of the carboxylic acid group is hydrogen) is lowered, and, as a result, the decomposability in water of the fibrous sheet is increased.

Specifically, the water-insoluble carboxymethyl cellulose serves as a binder in the fibrous sheet in dry condition.

Therefore, in comparison with a fibrous sheet not containing the water-insoluble carboxymethyl cellulose, the fibrous sheet for use in the invention has an increased surface strength and an increased breaking strength in the direction of the thickness. On the other hand, when the backsheet 12 made of this fibrous sheet has received a large amount of water, the water-insoluble carboxymethyl cellulose therein swells to cause strength reduction (i.e., lower the strength-retaining ability) of the fibrous sheet, so that the fibrous sheet is readily degraded even by a little force (of water streams). The decomposability in water of the fibrous sheet referred to herein is equal to the dispersibility in water thereof, and it means that, when the fibrous sheet has received a large amount of water, the fibers constituting the fibrous sheet are separately dispersed in water and, as a result, the fibrous sheet falls into small pieces therein.

In order that the fibrous sheet has good dry strength and good wet strength, the blend ratio of the water-insoluble carboxymethyl cellulose therein preferably falls between 1 and 30% by weight, more preferably between 3 and 10% by weight. If the blend ratio of the water-insoluble carboxymethyl cellulose therein is larger than 30% by weight, the decomposability in water of the fibrous sheet will be low, and the texture thereof will be degraded.

Preferably, the basic weight (Metsuke) of the fibrous sheet falls between 10 and 50 g/m$^2$. If it is smaller than the lowermost limit of the defined range, the backsheet made of the fibrous sheet could not have enough strength. On the other hand, if it is larger than the uppermost limit thereof, the fibrous sheet will lose a soft feel. More preferably, the basic weight of the fibrous sheet falls between 15 and 35 g/m$^2$.

The fibrous sheet for use in the invention may be made from the above-mentioned water-dispersible fibers and water-insoluble carboxymethyl cellulose in various production methods. For example, in one production method, water-dispersible fibers and water-insoluble carboxymethyl cellulose are mixed and made into a fibrous web according to a paper-making process to be formed into a water-decomposable paper. Alternatively, in another production method, water-dispersible fibers and water-insoluble carboxymethyl cellulose are mixed and made into a fibrous web, and then the resulting fibrous web is processed with water jets to be into a water-decomposable nonwoven fabric. In case where the backsheet 12 is made of the fibrous sheet having been subjected to such water-jetting treatment, it is bulky and will have a smooth feel. In this case, the thickness of the fibrous sheet could be, for example, 0.1 mm or more.

Furthermore, in case where the backsheet 12 is made of the nonwoven fabric as set forth above, the adhesive layer 30 can be firmly bonded to a rough surface of the nonwoven fabric owing to the anchor effect thereof. Accordingly, when the absorbent article is, after used, removed from the external support, the adhesive layer 30 can be readily released from the surface of the external support with keeping firm bonding to the backsheet 12, thereby hardly remaining on the surface of the external support.

In the invention, water-insoluble carboxymethyl cellulose of a completely-substituted type is used as a binder in the fibrous sheet. Therefore, when the fibrous sheet is, after made according to a paper-making process or after processed with water jets, heated and dried to remove water therefrom, its decomposability in water is not degraded under heat in the drying treatment.

In the processes of two production methods of the fibrous sheet as set forth above, when the water-dispersible fibers and water-insoluble carboxymethyl cellulose as a binder are mixed, the water-insoluble carboxymethyl cellulose is beaten or dissociated to further increase the degree of swellability in water, so that the strength of the fibrous sheet produced will be increased. Accordingly, by controlling the time and the machine force in mixing the fibers and the binder, it becomes possible to obtain the fibrous sheets having higher strength.

The water-jetting treatment to be applied to the fibrous web to obtain fibrous sheet for use herein will be described in detail. The fibrous web is put on a mesh conveyor belt sequentially feeding the fibrous web, and high-pressure water jets are applied thereto so as to pass through the fibrous web from the top surface to the back surface thereof. Through the water-jetting treatment, the properties of the nonwoven fabric obtained is to vary, depending on the basic weight of the fibrous web to be processed, the orifice size of the jetting nozzle to be used, the number of orifices of the nozzle, the processing speed of the fibrous web, and the like. Preferably, fibrous webs are subjected to water-jetting treatment, of which the work function (work load) represented by the following equation falls between 0.04 and 0.5 (kW/m$^2$) in one pass for one side surface of one fibrous web, once or repeatedly up to 6 times to obtain preferable nonwoven fabrics. The equation for deriving the work function is as follows:

Work function (kW/m$^2$)={1.63×jetting pressure (kg/cm)×jetting flow rate (m$^3$/min)}÷processing speed (m/min)

If the work function of the water-jetting treatment is larger than the uppermost limit of the defined range, the fibers constituting the fibrous web will be too much entangled during the treatment, and, as a result, the decomposability in water of the fibrous sheet produced may be degraded or the fibrous web being processed may be broken. On the other hand, if the work function is smaller than the lowermost limit of the defined range, the fibrous sheet produced could not have the desired strength.

However, even when the work function of the water-jetting treatment to be employed is not included in the range set forth above, it may be possible to obtain nonwoven fabrics having the desired strength and good decomposability in water by appropriately controlling the condition for water-jetting treatment and selecting suitable fibers for the fibrous web, etc.

Preferably, the fibrous sheet in dry has a breaking strength of at least 9.8 N/25 mm relative to the tensile load applied thereto in the direction of sheet surface (in a horizontal direction of the sheet). Also preferably, the fibrous sheet has a breaking strength of at least 1.5 N/18 mm in the direction of the thickness (in a vertical direction of the sheet). In addition, in order that the fibrous sheet having the preferred breaking strength can be readily decomposed in water in flush toilets, it is desirable that the decomposability in water of the fibrous sheet in wet is at most 120 seconds measured according to JIS P4501.

Not interfering with the effect of the invention, the fibrous sheet may contain any other compounds. For example, it may contain colorant, surfactant, microbicide, preservative, deodorizer, moisturizer, alcohol, etc.

The fibrous sheet may contain any other binder in addition to water-insoluble carboxymethyl cellulose in order to increase the strength thereof. The additional binder includes, for example, polyvinyl alcohol, modified polyvinyl alcohols such as carboxylic acid-modified polyvinyl alcohol and sulfonic acid-modified polyvinyl alcohol, alkyl celluloses such as methyl cellulose, as well as starch, modified starch, sodium polyacrylate, sodium alginate, polyethyleneoxide, etc.

If desired, the rear surface (the garment facing surface) of the backsheet 12 may be coated with a water-soluble resin such as polyvinyl alcohol or a copolymer comprising an unsaturated carboxylic acid to make the backsheet impervious to liquid.

As shown in FIG. 4, the adhesive layer 30 is formed on the rear side of the absorbent article 1. Concretely, the adhesive layer 30 is formed on the entire surface of the rear surface (the garment facing surface) of the backsheet 12 in a polka dot-pattern in which a number of dots are spotwise formed. The respective dots are substantially circular, preferably having a diameter of from 1 mm to 10 mm. The number of the dots are spaced from each other at an interval in both the longitudinal direction (direction Y) and the transverse direction (direction X) on the rear surface of the backsheet 12. Preferably, the dots of the adhesive layer 30 are aligned regularly in both the longitudinal direction and the transverse direction. Also preferably, the dots are substantially formed in the entire region of the rear surface of the backsheet 12.

The pattern of the adhesive layer 30 is not limited to the dots as illustrated, but may form stripes or rectangles regularly aligned in both the longitudinal direction and the transverse direction. Preferably, the area ratio of the dots of the adhesive layer 30 accounts for from 10 to 50% or so relative to the total area of the back of the backsheet 12.

The adhesive to form the adhesive layer 30 may be any and every one generally used as securing means for fitting the absorbent articles to the external supports. Especially preferred for it is a water-swellable adhesive of an acrylic or aqueous emulsion comprising a hydrophilic protective colloid, or polyvinyl alcohol.

The thermoplastic resin layer 12r formed on the absorbent core side of the backsheet 12 is, for example, a water-soluble or water-swellable polyvinyl alcohol film, and this is laminated on the backsheet 12.

The adhesives 13a and 13b provided in the intermediate region 1a are soluble or swellable in water, for which, for example, used is a hot-melt adhesive of polyvinyl alcohol.

The absorbent core 11 is made of, for example, water-decomposable paper, pulp or nonwoven fabric. For example, air-laid pulp is formed into the absorbent core 11, having a basic weight of from 50 to 70 g/m$^2$ or so. In case where the absorbent core 11 is formed of water-decomposable paper, it is desirable that a plurality of relatively thin water-decomposable papers are laminated to form it, as the absorbent core 11 thus formed is well decomposable in water. For example, from 4 to 8 sheets or so of water-decomposable paper having a basic weight of from 10 to 20 g/m$^2$ are laminated to form the absorbent core 11. If desired, the water-decomposable paper to be laminated to form the absorbent core may be coated with a water-swellable resin such as polyvinyl alcohol.

The topsheet 10 is, for example, made of a water-decomposable spun-laced nonwoven fabric. If desired, a plurality of water-decomposable papers may be laminated on such a water-decomposable nonwoven fabric to form the topsheet 10. In this case, the nonwoven fabric and a plurality of water-decomposable papers may be integrated through hydrogen bonding or needling. In order to lead excretions to the underlying absorbent core 11, it is desirable that a number of perforations are formed in the entire region of the topsheet 10 as shown in FIG. 1.

The water-decomposable absorbent article of the invention is described hereinabove with reference to one embodiment of pantiliners or sanitary napkins, to which, however, the invention is not limited. Needless to say, the absorbent article of the invention is applicable to any others such as disposable diapers and incontinence pads.

EXAMPLES

The invention will be described in more detail with reference to the following Examples, which, however, are not intended to restrict the scope of the invention.

In the following Examples, fibrous sheets to form the backsheet of the absorbent article of the invention were produced and tested for their physical properties. Precisely, softwood bleached kraft pulp (NBKP: CSF=600 cc), rayon (1.1 dtex, fiber length of 5 mm), and completely-substituted, water-insoluble carboxymethyl cellulose (CMC: carboxymethyl cellulose Kikkorate manufactured by Nichirin Chemical Industries, LTD., D.S.=0.43, pH=6.7, It should be noted that the hydrogens of the the carboxylic acid group in this CMC are completely 100% substituted with Ca or Na) were mixed in water in the mixture ratio indicated in Table 1 below. The stock of the resulting mixture was made into a fibrous web, which was then processed with water jets. Fibrous sheets thus produced provide Examples 1 to 3.

On the other hand, comparative fibrous sheets were produced in the same manner as above. For these, however, CMC was not used to provide Comparative Example 1. A fibrous binder of PVA (polyvinyl alcohol) was used in place of CMC to provide Comparative Example 2. The fibrous sheets of Examples 1 to 3 and Comparative Examples 1 and 2 were tested according to the methods mentioned below. The results are given in Table 1.

Decomposability in Water

The samples were tested according to the water-decomposability test of toilet paper in JIS P-4501. Precisely, each sample was cut to have a length of 10 cm and a width of 10 cm, put into a beaker filled with 300 ml of ion-exchanged water, and stirred therein with a stirrer. The revolution speed of the stirrer was 600 rpm. While stirred, the condition of the sample being dispersed in water was macroscopically observed at predetermined time intervals, and the time until the sample was dispersed was measured. In Table 1, the time is in terms of seconds.

Dry Strength

Each sample was cut to have a width of 25 mm and a length of 150 mm. These were tested by use of a Tensilon tester, for which chuck-to-chuck distance was 100 mm and the stress rate was 100 mm/min. The dry strength of the sample was measured both in the longitudinal direction (MD: machine direction) and in the transverse direction (CD: cross direction) thereof. In Table 1, the data are in terms of N/25 mm.

Surface Strength

According to the test method of using wax in JIS P8129-1976 2.1, the surface strength of each sample was measured. In Table 1, the data are in terms of the number of wax. In the test method, the waxes such as Dennison wax were fused to the surface of each sample. Sequentially increasing numbers were previously applied to the respective waxes depending on their adhesiveness. After fusion, the waxes were left to stand for cooling, and then peeled from the surface of the sample promptly. The largest number of the wax which caused no damage such as breakage on the surface of the sample was recorded as surface strength of the sample.

Breaking Strength in Thickness Direction

An polyester adhesive tape ("No. 31B75-HAI" manufactured by Nitto Denko Corporation) having a size of 18 mm×15 mm was attached onto both surfaces of the sample to be tested. Next, a one-kg roller was rolled on one tape surface of the sample at a speed of 5 m/min to apply load for securing the two tapes onto the sample. After that, the two tapes were vertically peeled away from each other at a stress rate of 100 mm/min, and the tensile strength at which the sample was separated (broken) in the direction of the thickness (specifically, in the vertically opposite directions) was measured.

In addition, pantiliners as shown in FIGS. 1 to 4 were produced, in which the backsheet 12 was made of the fibrous sheet of Examples 1 and 3. The pantiliners had a length of 140 mm and a width of 55 mm. In these, the topsheet 10 was made of a wet spun-laced nonwoven fabric having a basic weight of 45 $g/m^2$ and the absorbent core 11 was made of air-laid pulp having a basic weight of 60 $g/m^2$. An acrylic emulsion was used as an adhesive layer for fitting the pantiliner to an undergarment, and applied in polka-dot pattern.

The pantiliners were tried by 10 monitors for 8 hours. After that, the pantiliners were peeled from their undergarments, and checked as follows. The samples of Comparative Examples 1 and 2 were also tested in the same manner as above.

Wear Test (for adhesive transfer)

After tried, the pantiliners were peeled, and the undergarments were checked for a rate of occurrence of adhesive transfer on the undergarments. The data (the rate of occurrence) in Table 1 was derived from the following equation.

{(frequency of adhesive transfer)/10 (monitors)}×100

The data are in terms of %.

Wear Test (for backsheet breakage)

After tried, the pantiliners were peeled, and the undergarments were checked for a rate of occurrence of fiber residuals from the backsheet on the undergarments. The data (the rate of occurrence) in Table 1 was derived from the following equation.

{(frequency of fiber residuals)/10 (monitors)}×100

The data are in terms of %.

As set forth above in detail, the backsheet of the water-decomposable absorbent article of the invention is well decomposable in water and has high surface strength and high breaking strength in the direction of the thickness. Therefore, while used, the absorbent article well retain the shape thereof and is highly durable. Furthermore, when the absorbent article is fitted to an external support via the adhesive layer formed on the rear side of the backsheet and after used, it is peeled from the external support, the backsheet is hardly separated from the body of the absorbent article to avoid remaining on the external support.

In particular, in case where the backsheet is made of a water-decomposable nonwoven fabric processed with water jets, the absorbent article having been fitted to an external support can be smoothly peeled from the external support without leaving the adhesive layer on the external support. In this case, the adhesive layer can be well peeled from the external support in the condition of still firmly bonding to the backsheet.

While the invention has been described in detail and with reference to specific embodiments thereof, it will be apparent to one skilled in the art that various changes and modifications can be made therein without departing from the spirit and scope thereof.

What is claimed is:

1. A water-decomposable absorbent article, comprising:
a water-decomposable backsheet having two ends,
a water-decomposable liquid-pervious topsheet having two ends different from the two ends of said backsheet,
a water-decomposable absorbent core sandwiched between the backsheet and the topsheet, and
a water-swellable adhesive layer provided on a garment facing surface of the backsheet for securing the absorbent article to a garment, the adhesive layer being formed in a predetermined pattern to occupy 10 to 50% of the garment facing surface of the backsheet,
the backsheet being formed of a spunlaced nonwoven fabric having a basic weight within the range from 10 to 50 $g/m^2$, the nonwoven fabric comprising water-dispersible fibers having a length of at most 20 mm and

TABLE 1

|  |  | Example 1 | Example 2 | Example 3 | Comp. Ex. 1 | Comp. Ex. 2 |
|---|---|---|---|---|---|---|
| NBKP (beaten) |  | 90 | 92 | 85 | 80 | 90 |
| 1.1 dtex × 5 mm rayon |  | 5 | 5 | 5 | 20 | 5 |
| CMC |  | 5 | 3 | 10 | — | — |
| PVA fiber binder |  | — | — | — | — | 5 |
| Basic weight | $g/m^2$ | 25.2 | 25.5 | 25.4 | 24.8 | 25.1 |
| Thickness | mm | 0.120 | 0.118 | 0.122 | 0.125 | 0.116 |
| Decomposability in water | Sec | 65 | 55 | 105 | 30 | 300 or more |
| Dry strength (MD) | N/25 mm | 20.7 | 17.2 | 35.5 | 18.8 | 18.5 |
| Dry strength (CD) | N/25 mm | 15.6 | 12.3 | 18.8 | 13.9 | 14.1 |
| Surface strength | wax number | 6 | 5 | 8 | 2 | 2 |
| Breaking strength in thickness direction | N/18 mm | 2.1 | 1.8 | 3.8 | 1.2 | 3.0 |
| Wear test (for adhesive transfer) | % | 0 | — | 0 | 70 | 60 |
| Wear test (for backsheet breakage) | % | 0 | — | 0 | 20 | 10 |

As a result of the wear tests, as shown in Table 1, it could be understood that the samples of the invention having a surface strength, in terms of the number of wax, of more than 4 and having a breaking strength in the direction of the thickness of more than 1.5 N/18 mm, did not leave the adhesive and the backsheet fibers on the monitors' undergarments.

water-insoluble carboxymethyl cellulose having a degree of etherification within the range from 0.43 to 0.6 and being modified so that hydrogens of at least 95% of carboxylic acids therein are substituted with metal, a content of the water-insoluble carboxymethyl cellulose being from 1 to 30% by weight of the nonwoven fabric, the nonwoven fabric having a surface strength of at least 4 in terms of wax number, a breaking strength of at least 9.8 N/25 mm relative to a tensile load applied thereto in a horizontal direction of the sheet, a breaking strength of at least 1.5 N/18 mm in a vertical direction, and a water-decomposability of at most 120 seconds.

2. The absorbent article as set forth in claim 1, wherein the metal is at least one selected from the group consisting of calcium, sodium, magnesium, zinc, manganese, lithium, barium, and aluminum.

3. The absorbent article as set forth in claim 1, wherein the water-dispersible fibers are fibers of at least one selected from the group consisting of pulp, regenerated cellulose, abaca, and linter pulp.

4. The absorbent article as set forth in claim 1, wherein a water-soluble thermoplastic resin layer is applied to the absorbent side of said backsheet.

5. The absorbent article as set forth in claim 1, wherein the garment facing surface of said backsheet is liquid-impervious and coated with a water-soluble resin.

6. A water-decomposable absorbent sanitary napkin, comprising:

a water-decomposable backsheet having two ends, a water-decomposable liquid-pervious topsheet having two ends different from the two ends of said backsheet, a water-decomposable absorbent core sandwiched between the backsheet and the topsheet, and a water-swellable adhesive layer provided on a garment facing surface of the backsheet for securing the sanitary napkin to a garment, the adhesive layer being formed in a predetermined pattern to occupy 10 to 50% of the garment facing surface of the backsheet, the backsheet being formed of a spunlaced nonwoven fabric having a basic weight within the range from 10 to 50 g/m$^2$, the nonwoven fabric comprising water-dispersible fibers having a length of at most 20 mm and water-insoluble carboxyethyl cellulose having a degree of etherification within the range from 0.43 to 0.6 and being modified so that hydrogens of at least 95% of carboxylic acids therein are substituted with metal, a content of the water-insoluble carboxyethyl cellulose being from 1 to 30% by weight of the nonwoven fabric, the nonwoven fabric having a surface strength of at least 4 in terms of wax number, a breaking strength of at least 9.8 N/25 mm relative to a tensile load applied thereto in a horizontal direction of the sheet, a breaking strength of at least 1.5 N/18 mm in a vertical direction, and a water-decomposability of at most 120 seconds.

* * * * *